United States Patent [19]

McLean et al.

[11] Patent Number: 5,681,945
[45] Date of Patent: Oct. 28, 1997

[54] COMPOUNDS

[75] Inventors: Michael Joseph McLean, Nantwich; Andrew John Garman, Ashton, both of England

[73] Assignee: Zeneca Limited, London, United Kingdom

[21] Appl. No.: 41,591

[22] Filed: Apr. 5, 1993

[30] Foreign Application Priority Data

Apr. 3, 1992 [GB] United Kingdom .................. 9207380

[51] Int. Cl.$^6$ .................. C07H 19/04; C07H 21/02; C07H 21/00

[52] U.S. Cl. .................. 536/25.34; 536/25.3; 536/25.6; 536/26.1

[58] Field of Search ............... 536/25.3, 25.6, 536/26.1, 25.34

[56] References Cited

U.S. PATENT DOCUMENTS

| | | | |
|---|---|---|---|
| 4,775,619 | 10/1988 | Urdea | 435/6 |
| 5,118,605 | 6/1992 | Urdea | 435/6 |
| 5,378,825 | 1/1995 | Cook et al. | 536/75.3 |
| 5,380,833 | 1/1995 | Urdea | 536/22.1 |

OTHER PUBLICATIONS

Sigma Chem Comp Catalogue T6647 p. 1487 Pub. 1990.
Watanabe et al "J. Chromatography" 207 (1981) 13–20.
Merck Index 10th Ed. 1983 #8928 Tannic Acid p. 1301.
Pierce 1989 Handbook & General Catalogue p. 45 Heparin on TSK HW–65W.
C.A. 110:173684 No19 (May 8, 1989) Dellinger et al.

Primary Examiner—Herbert J. Lilling
Attorney, Agent, or Firm—Cushman Darby & Cushman Intellectual Property Group of Pillsbury Madison & Sutro, LLP

[57] ABSTRACT

A support carrying a homocyclic or heterocyclic ring containing a first and second carbon atom wherein: (i) the first carbon atom is substituted by a nucleophilic group or a group convertible to a nucleophilic group on treatment with base; (ii) the second carbon atom is substituted by a hydroxy group, a hydroxy group protected by an acid labile protecting group, or a phosphate group substituted by an oligonucleotide; and (iii) the first and second carbon atoms are directly connected by a covalent bond; which is suitable for use in oligonucleotide synthesis. Methods for its preparation and use, and novel compounds for attachment to the support are described.

9 Claims, 1 Drawing Sheet

COMPOUNDS

This invention relates to a support carrying a homocyclic or heterocyclic ring suitable for use in oligonucleotide synthesis, its preparation and use, to a homocyclic or heterocyclic compound which may be attached to a support and to a support linked to an oligonucleotide through a group derived from the compound.

It is known to prepare oligonucleotides in a stepwise manner on a solid support carrying a terminal nucleoside. Typically a support is formed by attaching an organic spacer group to a carrier, for example to controlled pore glass (CPG). A known solid support is shown as Formula (A) below

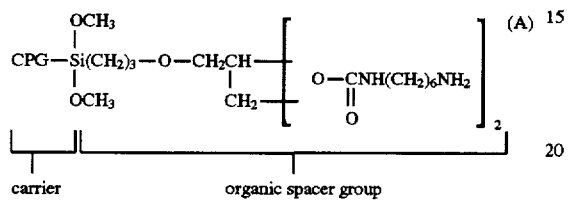

Before the above support can be used in oligonucleotide synthesis a nucleoside having a succinyl group is coupled to the terminal —NH$_2$ group, for example using 1,3-dicyclohexylcarbodiimide (DCCI).

The preparation and use of known solid supports in oligonucleotide synthesis has been fully described in a book by M. J. Gait entitled "Oligonucleotide Synthesis—A Practical Approach", IRL Press, revised reprinting July 1985; and also In the protocol to the Applied Biosystems DNA synthesiser Model 380B, particularly section 2 thereof which is incorporated herein by reference thereto. Further descriptions of how solid supports having a terminal nucleoside are made and used can be found in U.S. Pat. Nos. 4,458,066 and 4,725,677.

For automated oligonucleotide synthesiser operatives coupling of a nucleoside having a succinyl group to a support is considered inconvenient because this involves chemistry which differs from that used in such synthesisers and requires direct intervention by the operative, unlike the rest of the synthesis which is fully automated. For this reason the coupling is often not performed by the operative, instead operatives purchase a ready made support coupled to a nucleoside via a succinyl group.

A limitation of such a ready made support coupled to a nucleoside is that the nucleoside becomes part of the desired oligonucleotide when the oligonucleotide is cleaved from the support. Thus, for the synthesis of a given oligonucleotide one must take care to choose a support having an appropriate nucleoside attached to it which corresponds to the initial nucleoside in the desired oligonucleotide. This also means that an operative generally has to keep a number of different derivatised supports to cater for each of the different nucleosides found in DNA and RNA.

There is a need for a versatile derivatised support which is compatible with the chemistry used by synthesisers of oligonucleotides, which is compatible with both DNA and RNA synthesis irrespective of the first nucleoside in a desired oligonucleotide, and which can be used to prepare DNA or RNA having a non-nucleosidic terminal group. Furthermore, a derivatised support which can be used irrespective of the first group of a desired oligonucleotide would greatly reduce the likelihood of an operative inadvertently using a support derivatised with the wrong nucleoside.

A "universal" support has been suggested by Gough et al Tetrahedron Letters Vol 24 No. 48 pages 5321–5324. This support suffers from the disadvantage of having two free hydroxyl groups which produces a mixture of four products only one of which is the desired oligonucleotide product. Thus, the yield is severely limited and the applicants have found that it is difficult to separate the desired product from the complex mixture of oligonucleotides. Furthermore, the synthesis is long and complex and the cleavage method involves use of heavy metals which is not desirable.

The present invention provides the linkage to the support through a first carbon next to a second carbon which carries the free or protected hydroxyl so that only the desired product is formed.

According to a first aspect of the present invention there is provided a support carrying a homocyclic or heterocyclic ring containing a first and second carbon atom wherein:

(i) the first carbon atom is substituted by a nucleophilic group or a group convertible to a nucleophilic group on treatment with base;

(ii) the second carbon atom is substituted by a hydroxy group, a hydroxy group protected by an acid labile protecting group, or a phosphate group substituted by an oligonucleotide; and (iii) the first and second carbon atoms are directly connected by a covalent bond; and (iv) the homocyclic or heterocyclic ring is coupled to the support through the first carbon atom or through the nucleophilic group or group convertible to a nucleophilic group.

The preferred homocyclic or heterocyclic ring is a 5- or 6-membered ring, especially such a ring substituted by an electron withdrawing group. A preferred heterocyclic ring comprises or consists of 4 or 5 carbon atoms and one nitrogen, sulphur or oxygen atom. A particularly preferred heterocyclic ring is a pyran or furan ring, especially a pyran or furan ring free from double covalent bonds. As examples of homocyclic rings there may be mentioned cyclohexyl and cyclopentyl.

The identity of the support carrying the homocyclic or heterocyclic ring is not critical to the present invention. The support may be soluble in an organic solvent or may itself be a liquid, but is preferably a solid, more preferably a solid which is insoluble in an organic solvent. The preference for the support being a solid is because this can be packed into the column of an automated oligonucleotide synthesiser. The preferred soluble or liquid support is an organic polymer having little or no crosslinking, for example polyethylene glycol. The preferred support comprises a carrier and organic spacer group; said ring is connected to the organic spacer group. Alternatively said ring may be connected directly to the carrier.

The preferred carrier comprises an organic polymer or an inorganic polymer. A preferred organic polymer is a cellulosic substrate (for example a paper), a polystyrene, a polyacryloylmorpholide, a polyamide resin, a polyacryloyl pyrollidone, polyethylene glycol-polystyrene, or a cross-linked dextran or agarose. A preferred inorganic polymer is a silica, porous glass, aluminosilicate, borosilicate, or a clay, especially a controlled pore glass, a silica gel, Porasil C. Mixtures of inorganic and organic polymers may also be used, for example an acrylamide-kieselguhr resin, PEPSYN K or a POLYHIPE resin.

The length of the organic spacer group is not critical to the present invention. A preferred spacer group is at least 6, more preferably at least 8, especially at least 10 atoms long, and is preferably less than 100, more preferably less than 75, especially less than 30 atoms long. The preferred organic spacer group is straight or branched chain and preferably comprises a chain of methylene groups optionally interrupted by one or more carbonyl, amino, amide, ureido, urethane, ether, ester, silyl or aryl (e.g. phenylene) groups. In one embodiment the organic spacer group is free from phosphorus, particularly phosphate groups.

As examples of organic spacer groups there may be mentioned:

preferred ester groups containing less than 10 carbon atoms include esters of any dicarboxylic acid, for example, succinyloxy and oxalyloxy.

It is preferred that the ester group links the ring to the support. Preferably the group convertible to a hydroxy group on treatment with base is an ester formed between an acid on the support and a hydroxy group on the first carbon atom.

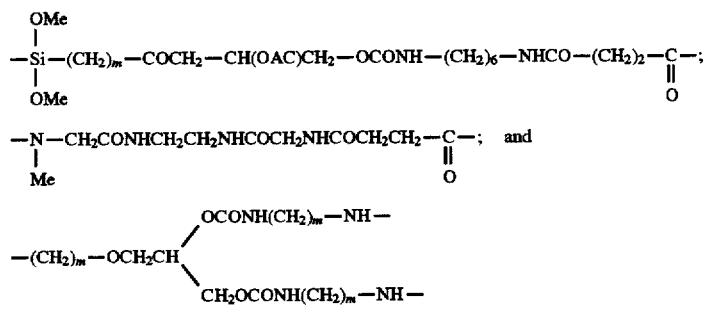

wherein each m independently has a value of from 2 to 6.

It is preferred that the second carbon atom on the homocyclic or heterocylic ring is substituted by a hydroxy group protected by an acid labile protecting group or a phosphate group substituted by an oligonucleotide. Suitable acid labile protecting groups will be apparent to those skilled in the art and include those acid labile groups discussed for protecting oxygen atoms in 'Protective Groups in Organic Synthesis' by T. W. Greene, Wiley Interscience. As will be appreciated the acid labile group is preferably sufficiently labile so that it may be removed under conditions which do not degrade DNA or RNA. Examples of preferred acid labile protecting groups include tetrahydropyranyl groups, e.g. tetrahydropyran-2-yl and 4-methoxytetrahydropyran-2-yl; optionally substituted trityl groups, for example a monomethoxytrityl for oligoribonucleotide synthesis and a dimethoxytrityl for oligodeoxyribonucleotide synthesis, pixyl; isobutyloxycarbonyl; t-butyl; and dimethylsilyl. The preferred acid labile protecting group is a dimethoxytrityl group, especially 4,4'-dimethoxytrityl.

Groups which are convertible to a nucleophilic group on treatment with base will be apparent to those skilled in the art. It is preferred that such groups are convertible to a nucleophilic group under conditions which do not degrade DNA or RNA. The preferred nucleophilic group is an amino, thio or especially hydroxy group.

Preferred conditions which do not degrade DNA or RNA include treatment with an inorganic base for example, sodium hydroxide, potassium hydroxide, ammonium hydroxide (conc), or an organic base (e.g. an organic amine, especially an alkylamine such as methylamine, triethylamine, diisopropylamine or a cyclic amine such as piperidine) at ambient or slightly elevated temperatures.

When the nucleophilic group is hydroxy, a preferred group which is convertible to a hydroxy group is an ester group which, on treatment with base, hydrolyses to give an acid, amide, (e.g. when hydrolysed with an amine) and a hydroxy group. Alternately the convertible group may be an ether group which, on treatment with a base, hydrolyses to give a hydroxy group. Formulae (1b) to (1d) illustrate the way in which the ring may be linked to the support by an ester group.

The ester group preferably contains less than 10 carbon atoms, more preferably less than 7 carbon atoms, and especially contains from 2 to 7 carbon atoms. Examples of In a second aspect of the present invention there is provided a support carrying a homocyclic or heterocyclic ring containing a first and second carbon atom wherein: (i) the first carbon atom is substituted by a nucleophilic group or a group convertible to a nucleophilic group on treatment with base; (ii) the second carbon atom is substituted by a hydroxy group, a hydroxy group protected by an acid labile protecting group, or a phosphate group substituted by an oligonucleotide; and (iii) the first and second carbon atoms are directly connected by a covalent bond; characterised by any one or more of (a) to (c) in which (a) the homocyclic or heterocyclic ring is not substituted with any of adenine, guanine, cytosine, thymine or uracil by direct attachment to the ring; (b) the substituents on the homocyclic or heterocyclic ring include no more than one hydroxy group; (c) the homocyclic or heterocyclic ring is optionally substituted with $C_{1-6}$ methoxy on carbon atoms other than the first and second carbon atoms.

The preferred embodiments are as previously described herein.

Terms used to describe the present invention can be more easily understood by reference to Formulae (1a) to (1d) below which provide illustrative examples of homocyclic and heterocyclic rings which may be carried by a support. In the Formulae $Z^1$ is an acid labile protecting group, A is a first carbon atom and B is a second carbon atom.

 (1a)

 (1b)

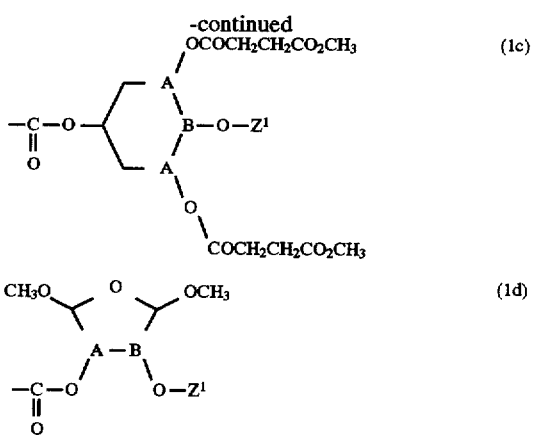

In Formula (1a) first carbon atom A is substituted by a nucleophilic hydroxy group, second carbon atom B is substituted by a hydroxy group protected by an acid labile protecting group and A and B are directly connected by a covalent bond.

In Formula (1b) first carbon atom A is substituted by a group convertible to a hydroxy group on treatment with base, second carbon atom B is substituted by a phosphate group substituted by an oligonucleotide, and A and B are directly connected by a covalent bond.

In Formula (1c) first carbon atom A is substituted by a group convertible to a hydroxy group on treatment with base, second carbon atom B is substituted by a hydroxy group protected by an acid labile protecting group, and A and B are directly connected by a covalent bond.

In Formula (1d) first carbon atom A is substituted by a group convertible to a hydroxy group on treatment with base, second carbon atom B is substituted by a hydroxy group protected by an acid labile protecting group, and A and B are directly connected by a covalent bond.

It will be appreciated, particularly in view of the above examples, that the term "substituted by" as used herein is intended to include both the coupling to the support being indirectly through a substituent on the homocyclic or heterocyclic ring or directly onto the ring itself. Similarly, the term "coupled . . . through" as used herein means coupled directly to the ring or indirectly by means of a bond formed with the substituent on the ring, as described above by formulae (1a) to (1d) and in more detail below. The term 'oligonucleotide' used in this specification includes oligoribonucleotides and oligodeoxyribonucleotides. The preferred oligonucleotides comprise at least 2, more preferably at least 5, especially at least 10 nucleosides, and preferably less than 1000, more preferably less than 500, especially less than 200 nucleosides. Preferably the oligonucleotide is attached to the second carbon atom through a phosphate ester group of formula —O—P(=O)(—OR$_6$)—O— or —O—P(=S)—(OR$_6$)—O— wherein R$_6$ is H or a phosphate protecting group.

The support carrying a ring where the second carbon atom is substituted by an oligonucleotide may be prepared from a support according to the invention in which the second carbon atom is substituted by a hydroxy group protected by acid labile protecting group, as will be apparent to those skilled in the art. It is preferred that the oligonucleotide is synthesised in the 3' to 5' direction. A support in which the second carbon atom is substituted by a dimethoxytrityloxy group may be packed into an oligonucleotide synthesiser column, and an oligonucleotide formed in a stepwise manner in an analogous way to that in which an oligonucleotide is formed on conventional derivatised supports, for example those of Formula (A) derivatised with a nucleoside succinate. For example, one takes the support according to the invention in which the second carbon atom is substituted by a dimethoxytrityloxy group and forms an oligonucleotide thereon using the known steps of 1. detritylation of the support, e.g. using trichloroacetic acid;
2. activation of a nucleoside phosphoramidite, e.g. with tetrazole;
3. addition of the phosphoramidite;
4. capping, e.g. using acetic anhydride; and
5. oxidation, e.g. using H$_2$O/I$_2$ or H$_2$O$_2$.

Steps 1 to 5 are repeated for each nucleoside phosphoramidite until the desired oligonucleotide has been obtained. At this stage the phosphates in the oligonucleotide chain are, where desired, deprotected and the oligonucleotide may be cleaved from the support using a base, preferably aqueous ammonia or methylamine at room temperature. As will be appreciated the oligonucleotide may be prepared using chemistry other than phosphoramidite chemistry.

If the cleavage step frees the oligonucleotide from the support but residues of the ring remain attached to the oligonucleotide by a phosphate ester group these may be removed by further treatment with base, for example by incubation therewith at 20°–80° C., especially 30°–70° C., for up to 48, especially 1 to 24 hours, to give an oligonucleotide having a 3' OH group.

The support carrying a homocyclic or heterocyclic ring in which the second carbon atom is substituted by an acid labile protecting group may be prepared by coupling a support and said homocyclic or heterocyclic ring, preferably by formation of an ester, amide or ether bond therebetween. The ester or amide bond is preferably formed by selecting one of either the ring or support to carry a hydroxy or amino group and the other to have an acid group, activating the acid, and coupling to form an ester or amide bond. It will be apparent to those skilled in the art how an acid may be activated, for example it may be converted to an acid halide (e.g. using SOCl$_2$) or an activated ester (e.g. an o-nitrophenyl ester using DCCI). Preferably coupling is performed in the presence of a base. As will be appreciated, the ring may be coupled to the support through a side chain on the ring having an acid, amino or hydroxy group, thereby effectively lengthening the spacer group.

A support according to the first aspect of the present invention where the second carbon atom is substituted by a hydroxy group may be prepared by deprotection of such a support where the second carbon atom is substituted by a hydroxy group protected by an acid labile protecting group, for example using Cl$_3$CO$_2$H.

A preferred support according to the invention carries a group of Formula (2):

wherein A and B are carbon atoms of an optionally substituted 5- or 6-membered ring and are directly connected by a covalent bond; Z$^2$ is H, an acid labile protecting group or a phosphate group substituted by an oligonucleotide; and n is 0 or 1; provided that when n is 0 there is a hydroxy group or a group which is convertible to a hydroxy group on treatment with base on a carbon atom directly connected to B by a covalent bond.

Formula (1a) above shows one example of a hydroxy group on a carbon atom directly attached to B by a covalent bond.

It is preferred that n is 1.

The preferred groups which are convertible to a hydroxy group on treatment with base are as hereinbefore described.

It is preferred that A and B are carbon atoms of a 5- or 6-membered homocyclic or heterocyclic ring and are directly connected by a covalent bond. Preferred homocyclic and heterocyclic rings are as hereinbefore described.

The substituents which may be present on the 5- or 6-membered ring of which A and B are adjacent carbon atoms are preferably selected from hydroxy; a group convertible to hydroxy on treatment with base; straight or branched chain $C_{1-6}$-alkyl, especially methyl, ethyl, propyl, butyl or tertiary butyl; $C_{1-6}$-alkoxy, especially methoxy, ethoxy, propoxy and butoxy, particularly methoxy; aryloxy, especially optionally substituted phenoxy; halogen, cyano, nitro, optionally protected oxycarbonyl, thio or amino or a group which is convertible to a thio or amino group on treatment with base, or an electron withdrawing group.

As examples of groups convertible to thio or amino on treatment with base there may be mentioned thioesters, carbamates and amides such as trifluoracetamide.

Preferred groups of Formula (2) are illustrated by Formulae (1b) and (1d) above. It is particularly preferred that the 5- or 6-membered ring has one or two $C_{1-4}$-alkoxy substituents as these may assist cleavage of the oligonucleotide from B at the end of synthesis thereof.

The support carrying the group of Formula (2) wherein $Z^2$ is an acid labile protecting group may be prepared, for example, by coupling a support containing an organic spacer group having a terminal hydroxyl or amino group with a compound of the Formula (3):

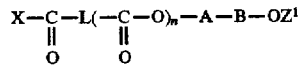   (3)

wherein X is HO or a leaving group; L is an organic linking group; and A, B, $Z^1$ and n are as hereinbefore defined.

The preferred leaving group represented by X is a halide, especially chloride, or the residue of an activated ester, for example o-nitrophenoxy, or an anhydride. Suitable conditions for the coupling reaction will be apparent to those skilled in the art. It is preferred that the coupling is performed in an aprotic solvent, especially in the presence of a base. DCCI may be used to make an activated ester.

The preferred organic linking group represented by L is from 1 to 20 carbon atoms long, more preferably 2 to 6 carbon atoms long. It is preferred that L is phenylene or $-(CH_2)_p-$ where p is from 2 to 6, especially 2.

A particularly preferred compound of the invention is Formula (4):

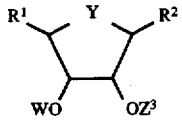

wherein Y is S, NH, O, $CH_2$ or $CH_2CH_2$; $R_1$ and $R_2$ are each independently H; hydroxy, thio or amino, or a group convertible to a hydroxy, thio or amino group on treatment with base; alkyl, especially $C_{1-6}$-alkyl; alkoxy, especially $C_{1-6}$-alkoxy; or aryloxy, especially optionally substituted phenoxy, halogen, cyano, nitro, optionally protected oxycarbonyl or an electron withdrawing group; W is H or

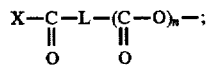

and $Z^3$ is hydrogen or an acid labile protecting group or a group of formula

wherein Oligo is an oligonucleotide, provided that when $Z^3$ is

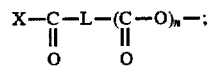

$R_6$ is H or a protecting group, for example as hereinafter described for $R_6$; and X, L and n are as hereinbefore defined.

It is preferred that Y is O, $CH_2$ or $CH_2CH_2$.

$Z^3$ is preferably an acid labile protecting group as hereinbefore described.

When W is H, this compound is an intermediate which can be reacted with a compound such as X—C(=O)—L—C(=O)—Cl or the anhydride of the free acid thereof to form the compound of formula (4) in which W is X—C(=O)—L—(C(=O)—O)$_n$.

An alternative method for preparing a derivatised support according to the invention is to condense a support comprising a carrier and organic spacer group, wherein the organic spacer group has an amino, thio or hydroxy group, with a compound of Formula (5):

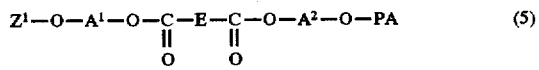   (5)

wherein —O—PA is a phosphoramidite group, phosphate ester group or a H-phosphonate group; $A^1$ is a divalent group of the formula (a):

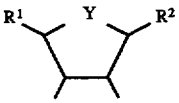

E is an organic spacer group; Y, $Z^1$, $R^1$ and $R^2$ are as hereinbefore defined; and $A^2$ is of formula (a) or formula (b):

wherein m has a value of from 1 to 5; the carbon atom marked with an asterisk is attached to an oxygen atom shown in Formula (5); and each $R^3$ independently represents H or optionally substituted alkyl.

Preferably $A^1$ and $A^2$ are both of Formula (a) and m preferably has a value of from 1 to 3, more preferably 2.

The preferred carrier, organic linking group, acid labile group and groups represented by Y, $R^1$ and $R^2$ are as hereinbefore defined.

E is preferably an organic spacer group having a length of 2 to 15 carbon atoms, more preferably 2 to 6 carbon atoms. E is preferably an alkyl, alkenyl, aryl or aralkyl spacer group optionally interrupted by an oxygen, sulphur, amino or amido group. Preferred groups represented by E are optionally substituted phenylene and $C_{2-6}$-alkylene, especially —CH$_2$—CH$_2$—. R$^3$ is preferably H or C$_{1-4}$-alkyl, especially H. As examples of groups represented by formula (b) there may be mentioned —*CH$_2$CH$_2$—SO$_2$—CH$_2$—CH$_2$— and —*CHCH$_3$—CH$_2$—SO$_2$—CH$_2$—CH$_2$—.

As examples of phosphate ester groups and H-phosphonate groups there may be mentioned groups which, in the free acid form, are respectively of formula:

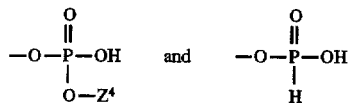

wherein Z$^4$ is a base labile protecting group, for example 2-chlorophenyl or 2,4-dichlorophenyl.

The preferred phosphoramidite group represented by —O—PA is of the formula:

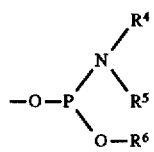

wherein R$_4$ and R$_5$ are each independently optionally substituted alkyl, especially C$_{1-4}$-alkyl; optionally substituted aralkyl, especially optionally substituted benzyl; cycloalkyl and cycloalkylalkyl containing up to ten carbon atoms, such as cyclopentyl or cyclohexyl; or R$_4$ and R$_5$ taken together with the nitrogen atom to which they are attached form an optionally substituted pyrollidine or piperidine ring or R$_4$ and R$_5$ when taken together with the nitrogen atom to which they are attached form a saturated nitrogen heterocycle which optionally includes one or more additional hetero atom from the group consisting of nitrogen, oxygen and sulphur. R$_4$ and R$_5$ are preferably iso-propyl.

R$_6$ represents a hydrogen atom or a protecting group, for example a phosphate protecting group. As examples of phosphate protecting groups there may be mentioned optionally substituted alkyl groups, for example methyl, 2-cyanoethyl, 2-chlorophenyl, 2,2,2-trihalo-1,1-dimethyl ethyl, 5-chloroquin-8-yl, 2-methylthioethyl and 2-phenylthioethyl groups in which the phenyl ring is optionally substituted, for example by a group selected from halogen, eg. chlorine, or NO$_2$. Preferably R$_6$ is methyl or, more preferably, 2-cyanoethyl.

As will be appreciated the compounds of the present invention can exist in either the cis or trans form. However, the trans form of the compounds demonstrate a slower rate of cleavage and therefore result in oligonucleotides bearing terminal organic phosphate groups which may find applications in situations where the termini are required to be blocked.

Also as will be appreciated when a compound of Formula (5) is condensed with a support part of the compound attached to A$^1$ (shown to the right of A$^1$ in Formula (5)) becomes part of the organic spacer group.

The compound of Formula (5) may be condensed with said amino, thio or hydroxy group by activating —O—PA, e.g. with tetrazole, condensing with the support, capping, e.g. with acetic anhydride, and if desired oxidising with H$_2$O/I$_2$ or H$_2$O$_2$.

Compounds of Formula (5) wherein —O—PA is a phosphoramidite may be prepared by reacting a compound of formula

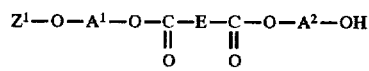

with a compound of formula X$^1$-PA in CH$_2$Cl$_2$ using di(N-isopropyl)ethylamine as base. PA is preferably a phosphoramidite as defined above for —O—PA except that —O— is absent, and Z$^1$, A$^1$, E and A$^2$ are as hereinbefore defined, and X$^1$ is a leaving group, for example Cl or Br.

When —O—PA in Formula (5) is a phosphate ester group as hereinbefore defined the compound of Formula (5) may be prepared by reaction of a compound of formula

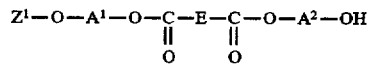

with the triazolide of the corresponding free phosphate ester using a method analogous to that described in the above book by M. J. Gait.

When —O—PA in Formula (5) is a H-phosphonate group as hereinbefore defined the compound of Formula (5) may be prepared by reaction of a compound of formula

Z$^1$—O—A$^1$—O—C—E—C—O—A$^2$—OH
‖ ‖
O O with PCl$_3$ in the presence of 1,2,4-triazole using a method analogous to that described by B. C. Froehler et al, Nucleic Acid Research, (1986), 14, 5399–5407.

The compound of formula

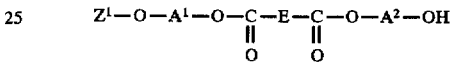

may be prepared, for example, by reaction of a compound of formula

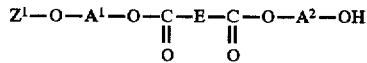

with a compound of formula HO—A$^2$—OH, preferably in an aprotic solvent using a suitable condensing agent such as the aforementioned DCCI or 1-(3-Dimethylaminopropyl)-3-ethylcarbodiimide.

The compound of formula Z$^1$—O—A$^1$—E—CO$_2$H may be prepared by the reaction of the compound of formula Z$^1$—O—A$^1$—OH with an activated form of the compound of formula HO$_2$C—E—CO$_2$H, preferably in an aprotic solvent in the presence of a molar equivalent of base. The dicarboxylic acid may be activated to attack by the hydroxyl group by being present as the acid anhydride, the acid chloride or some other suitable derivative, or the reaction may be mediated by the presence of a coupling agent as described above.

The compound of formula Z$^1$—O—A$^1$—OH may be prepared by the reaction of the compound of formula HO—A$^1$—OH with Z$^1$—Cl (or some other suitably activated form of Z$^1$) in an anhydrous aprotic solvent in the presence of a molar equivalent of base.

When A$^1$ is of Formula (a) shown above the compound of formula Z$^1$—O—A$^1$—OH is preferably prepared by debenzoylation of a compound of formula Z$^1$—O—A$^1$—O—CO—Ph in methanol using methylamine. The compound of formula Z$^1$—O—A$^1$—O—CO—Ph may be prepared by reaction of compound of formula HO—A¹—O—CO—Ph with Z¹—X¹ wherein X¹ is a leaving group, for example Cl.

In the above processes for the preparation of the compound of Formula (5), and precursors thereof, $Z^1, A^1, E, A^2$, DCCI and —O—PA are as hereinbefore defined.

The derivatised support of the invention will be of particular value in automated oligonucleotide synthesisers which currently use several different types of column to cater for the different oligonucleotide a user may wish to prepare. Using the present invention only one universal derivatised support packed into a column is necessary thereby reducing the probability of error through an operative selective an inappropriate support.

BRIEF DESCRIPTION OF DRAWINGS

The following drawings further illustrate the invention wherein.

Figure 1A:
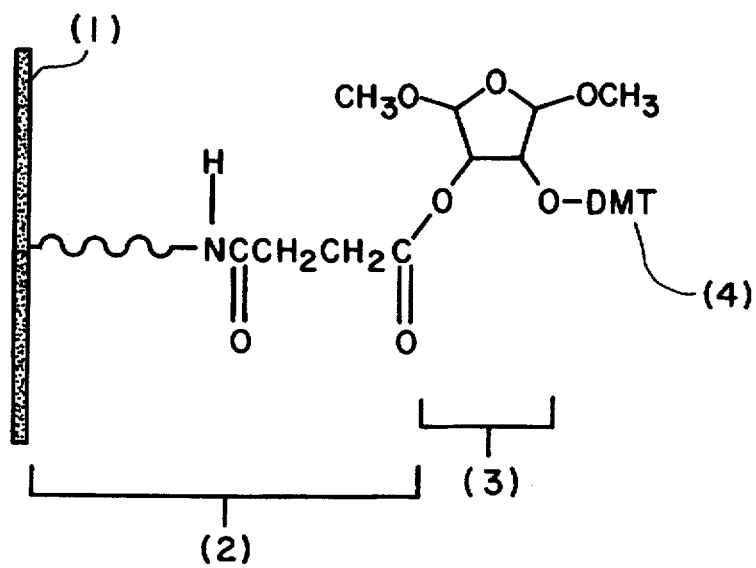
FIG. 1a shows a derivatised support according to the invention.

According to FIG. 1a heterocyclic ring (3) is protected by a 4,4¹-dimethoxytrityl group (4) and is carried by a support comprising carrier (1) and organic spacer group (2).

Figure 1B:
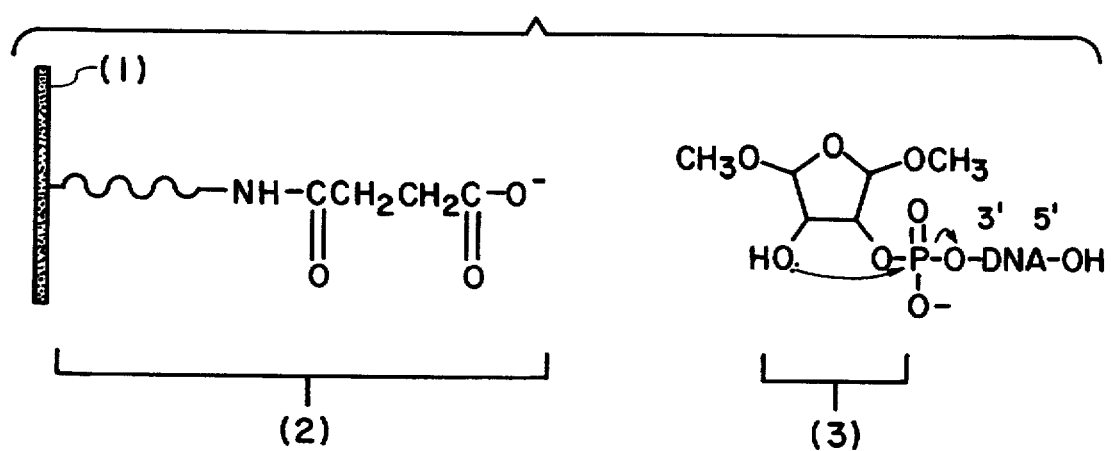
FIG. 1b shows the support from FIG. 1a after use.

FIG. 1b illustrates the support from FIG. 1a after it has been used to synthesise a strand of DNA, for example by using phosphoramidite chemistry. Treatment with ammonia has cleaved the heterocyclic ring (3) from the organic spacer group (2) and handle (1). Further treatment with base frees the DNA from the heterocyclic group (3) by a mechanism which is believed to be as illustrated, wherein a nucleophilic hydroxy group displaces DNA from the phosphate to give DNA having a 3' hydroxy group.

The invention is further illustrated by the following Examples in which all parts and percentages are by weight unless indicated otherwise.

EXAMPLE 1

Reagent A1 was prepared using the preparations numbered 1–4 detailed below.

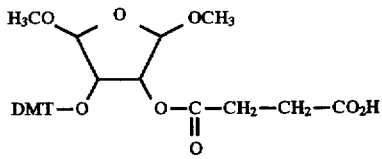

1) Preparation of r-3,Cis-4-dihydroxy-cis plus trans-2, -trans-5-dimethoxytetrahydrofuran

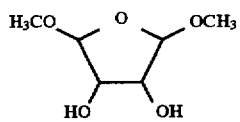

2,5-Dihydro-2,5-dimethoxyfuran (50g; Aldrich, cis/trans mixture) was dissolved in tetrahydrofuran (500ml) in a 5 litre, three-necked flask fitted with a mechanical stirrer. The contents of the flask were cooled to −5° C., and a solution of potassium permanganate (61.9 g) in water (2250 ml) was added dropwise with vigorous stirring at such a rate as to keep the temperature of the flask contents between 4° and 6° C. This addition took 80 minutes. The reaction mixture was then left stirring and allowed to warm to room temperature over 15 hours. The precipitated manganese dioxide was filtered off through Celite and washed with THF (200 ml).

The clear colourless filtrate was evaporated and the residue was shaken vigorously with ethyl acetate (200 ml) until no material adhered to the flask wall. The fine precipitate of KOH was filtered off on a glass sinter and washed with ethyl acetate. The filtrate was rotary evaporated to give the title compound as a golden syrup (24.4 g, 38.6%). The compound was mainly the meso product (80%) contaminated with the d1 compound (20%).

| ¹³C—NMR: | | |
|---|---|---|
| meso product | $\underline{C}H_3O$ | 55.462 ppm |
|  | $\underline{C}HOH$ | 75.303 ppm |
|  | $\underline{C}HOCH_3$ | 109.606 ppm |
| d1 product | $\underline{C}H_3O$ | 56.451 ppm |
|  | $\underline{C}HOH$ | 70.654 and 73.604 ppm |
|  | $\underline{C}HOCH_3$ | 103.155 and 108.257 ppm |

2) Preparation of

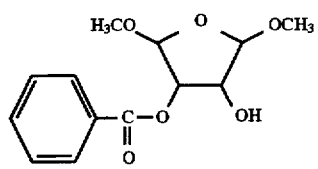

The product from step 1) above (1.7 g) was dissolved in dry pyridine (10 ml) and 4-N,N-dimethylaminopyridine (DMAP) (100 mg) was added. The mixture was swirled to dissolve the solid and benzoyl chloride (1.2 ml) was added. The mixture was then left to stand at 20° C. for 16 hours. The mixture was rotary evaporated, and residual pyridine was removed by repeated co-evaporation with toluene. The residual oil was partitioned between ethyl acetate and 1M HCl (40 ml of each). The organic layer was washed in succession with water, 1M NaHCO₃, and saturated brine (40 ml of each), dried over magnesium sulphate, filtered and rotary evaporated. The residual oil was redissolved in dichloromethane/methanol (19/1) and applied to a silica column. Elution with the same solvent gave the desired product as a white solid (1.11 g, 38%)

| ¹³C—NMR: | |
|---|---|
| $\underline{C}H_3O$ | 55.680 and 55.951 ppm |
| $\underline{C}HOH$ and $\underline{C}HOCO$ | 75.016 and 77.973 ppm |
| $\underline{C}HOCH_3$ | 107.136 and 109.899 ppm |
| $\underline{C}_6H_5$ | 128.576, 129.300, 129.957 and 133.952 ppm |
| $\underline{C}O$ | 166.076 ppm |

3) Preparation of

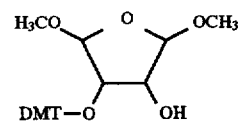

The product from step 2) above (2.47 g), 4,4'-dimethoxytrityl chloride (3.12 g) and DMAP (0.15 g) were stirred in dry pyridine (20 ml) at room temperature for 16 hours. The solvent was removed by rotary evaporation and residual pyridine was removed by repeated co-evaporation with toluene. The residue was partitioned between ethyl acetate and water (50 ml of each) and the organic layer was washed with 1M sodium bicarbonate, then saturated brine (20 ml of each), dried over magnesium sulphate, filtered and rotary evaporated to an oil which was dissolved in a solution of methylamine in methanol (120 ml, 7.5 M) and incubated at room temperature for 24 hours. The solution was filtered and the filtrate was evaporated to an oil which was redissolved in the minimum volume of petroleum (b.p. 60–80° C.)/ethyl acetate (3/2) and applied to a silica column. Elution with the same solvent gave the desired product (2.3 g) as a white foam which was used directly in the next step without further characterisation.

4) Preparation of Reagent A1

The product from step 3) above (2.28 g) was dissolved in dry pyridine (20 ml) and succinic anhydride (0.55 g) and DMAP (0.4 g) were added. The mixture was swirled to dissolve the solids and then left at room temperature for 16 hours. The solvent was removed by rotary evaporation and residual pyridine was removed by repeated co-evaporation with toluene. The residue was partitioned between ethyl acetate and 10% (w/v) citric acid (50 ml of each). The organic layer was washed with water then saturated brine (50 ml of each), dried over magnesium sulphate, filtered and rotary evaporated to an oil which was redissolved in the minimum volume of dichloromethane/methanol (19/1) and applied to a silica column. Elution with the same solvent gave the title compound as a colourless glass (1.98 g, 71.4%).

$^{13}$C-NMR: $\underline{C}$H2 groups of OC$\underline{C}$H$_2$$\underline{C}$H$_2$CO: 28.790 ppm and 28.939 ppm $\underline{C}$H$_3$OAr: 54.988 ppm $\underline{C}$H$_3$OCH×2: 55.251 ppm $\underline{C}$H$_3$OAr: 56.039 ppm $\underline{C}$HODMT and $\underline{C}$HOCO: 75.518 ppm and 76.424 ppm quat $\underline{C}$ of DMT: 87.194 ppm $\underline{C}$HOCH3: 106.572 ppm, 109.102 ppm Ar$\underline{C}$H : 113.245 ppm, 127.821 ppm, 128.337 ppm, 129.160 ppm, 130.250 ppm and 130.280 ppm Ar quat $\underline{C}$: 139.893 ppm, 136.035 ppm, 144.855 ppm and 158.859 ppm $\underline{C}$OO: 170.879 ppm $\underline{C}$OO 177.540 ppm

EXAMPLE 2

Coupling of Reagent A1 to controlled pore glass

Reagent A1 (60 mg) was dissolved in dioxan (4 ml) containing pyridine (0.2 ml) and o-nitrophenol (14 mg). To this solution was added 1,3-dicyclohexylcarbodiimide (51.5 mg) and the mixture was incubated at room temperature for 5 hours and then at 4° C. for 1 hour. The dicyclohexylurea was filtered off, and the filtrate was added to a suspension in dry dimethylformamide of controlled pore glass derivatized with a long chain alkylamine (CPG LCAA available from Cruachem) (particle size 120–177 um, primary amino loading of 215 μmole/g, pore diameter 500A, 100 mg). Triethylamine (0.1 ml) was added and a yellow colouration immediately developed. The reaction mixture was incubated at room temperature for 16 hours with occasional swirling. The mixture was filtered on a glass sinter, and the solid was washed extensively with DMF, methanol and diethyl ether and dried in vacuo.

The extent of loading of the support with reagent A1 was determined by treatment of 2 mg with perchloric acid followed by spectrophotometric determination of the dimethoxytrityl cation as described by Atkinson and Smith in the book by M. J. Gait. By this method, the loading of the support with reagent A1 was 69.5 μmoles/g.

The support coupled with reagent A1 was suspended in a solution of acetic anhydride (1 ml) in dry pyridine (10 ml) containing DMAP (10 mg), and this mixture was incubated at room temperature for 30 minutes. The mixture was filtered on a glass sinter, washed extensively with methanol and diethyl ether and dried overnight in vacuo.

The resultant product was a support carrying a group of Formula:

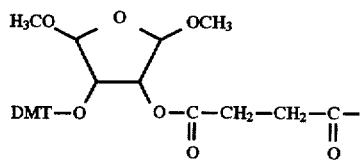

As will be appreciated the right hand side is connected to CPG via an organic spacer group.

EXAMPLE 3

Coupling of Reagent A1) to polystyrene

The method of Example 2) was repeated, except that in place of the controlled pore glass derivatised with a long chain alkylamine used in Example 2), there was used aminomethyl polystyrene (Applied Biosystems Inc.) (primary amino loading of 20 μmole/g, 100 mg).

The extent of loading of the support with Reagent A1 was determined by the method of Example 2). By this method, the loading of the support with Reagent A1 was 14 μmole/g.

The support coupled with Reagent A1 was suspended in a solution of acetic anhydride (1 ml) in dry pyridine containing DMAP (10 mg), and this mixture was incubated at room temperature for 30 minutes. The mixture was filtered on a glass sinter, washed extensively with methanol and diethyl ether, and dried overnight in vacuo.

The resultant product was a support carrying a group of Formula:

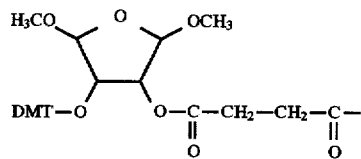

As will be appreciated, the right hand side is connected to polystyrene via an organic spacer group.

EXAMPLE 4

Synthesis of an oligonucleotide using the support from Example 2

A fully protected oligodeoxyribonucleotide of sequence (5') CAAGTTTTCAGTCAGCCGAGTTCAG (3') (SEQ ID NO: 1) was prepared as follows.

A column containing the product from Example 2 (3 mg) was attached to an Applied Biosystems 380B DNA synthesizer and the oligomer whose sequence is shown above was synthesized in a stepwise manner from nucleoside phosphoramidites using standard synthesis cycles, as fully described in the protocol to the synthesizer.

The oligonucleotide phosphoramidites used were the 2-cyanoethyl-N,N-diisopropylaminophosphoramidites of 5'-dimethoxytrityl-N$^4$-benzoyl-2'-deoxycytidine, 5'-dimethoxytrityl-N$^2$-isobutyryl-2'-deoxyguanosine, 5'-dimethoxytrityl-N$^6$-benzoyl-2'-deoxyadenosine and 5'-dimethoxytritylthymidine (Cruachem Ltd).

The duration of the reaction steps and the volume of reagents used for detritylation, activation of nucleoside phosphoramidites, addition of phosphoramidites, capping and oxidation were identical for each coupling, including that for detritylation of the derivatised support and coupling of the first nucleotide.

The detritylated oligodeoxyribonucleotide sequence was cleaved from the solid support by treatment with ammonium hydroxide (sp.gr. 0.88) on the synthesizer, and the ammoniacal solution was washed into a collection vial according to normal synthesizer protocols. Complete deprotection and removal of the terminal 3'-phosphate were performed by incubation of this solution at 55° C. for 16 hours.

A second oligonucleotide was synthesized by conventional procedures as described above but using a conventional support having a guanine containing nucleoside attached thereto. The sequence of this oligonucleotide was: (5') CAAGTTTTCAGTCAGCCGAGTTCAG (3')

Thus, the second oligonucleotide is of identical length and sequence to the product expected from using the support of the invention and removal of the terminal phosphate from the example described above.

Cleavage of the cleavable link and removal of the terminal (3') phosphate was demonstrated by analysis of the products of the reaction on denaturing polyacrylamide gel electrophoresis and location of the products by autoradiography as described below.

Incorporation of radiolabelled phosphate at the 5'-end of oligonucleotides

After treatment of the oligonucleotides with concentrated ammonium hydroxide the solutions were lyophilized and the oligonucleotides redissolved in water to a concentration of approximately 1 mg/ml. For each oligomer, one microlitre of this solution was then added to an Eppendorf tube containing water (6 µl), 10×reaction buffer ("One Phor All", Pharmacia, 1 µl), [gamma $^{32}$p]adenosine triphosphate (Amersham, 1u1) and T4 polynucleotide kinase (Pharmacia, 1 ul). This mixture was then incubated at 37° C. for one hour. Ethanol (30 ul) was then added, the contents were mixed by repeated inversion of the tube, and the sample was incubated at −70° C. for 15 minutes. The tube was spun in an Eppendorf centrifuge (Model 5415) at 14000 rpm for 15 minutes and the supernatant was discarded. The pellet was dried briefly in vacuo and was redissolved in 10 ul of a solution containing 80% formamide, 0.1% bromophenol blue, 0.1% xylene cyanol and 10 uM EDTA. This solution was loaded into one of the wells of a denaturing polyacrylamide gel (12% acrylamide, 50% urea) adjacent to the appropriate radiolabelled size marker, and the gel was run at 40 W for approximately two hours. The locations and sizes of labelled DNA fragments were determined by autoradiography.

The presence of a band having the same mobility as a band due to the oligonucleotide of 25 residues (24 phosphates) prepared by conventional methods on a conventional support indicated that the products from using the conventional support and the support from Example 2 were the same.

EXAMPLE 5

Synthesis of an oligonucleotide using the support from Example 3)

A fully protected oligodeoxyribonucleotide of sequence: (5') AAAA (3') was prepared using the method of Example 4), except that in place of a column containing the product from Example 2), there was used a column containing the product from Example 3).

The duration of the reaction steps and the volume of reagents used for detritylation, activation of nucleoside phosphoramidites, addition of phosphoramidites, capping and oxidation were identical for each coupling, including that for detritylation of the derivatised support and coupling of the first nucleotide.

The detritylated oligodeoxyribonucleotide sequence was cleaved from the solid support by treatment with ammonium hydroxide (sp.gr. 0.88) on the synthesiser, and the ammoniacal solution was washed into a collection vial according to normal synthesiser protocols. Deprotection and removal of the terminal 3'-phosphate were performed by incubation of this solution at 55° C. for 16 hours.

A second oligonucleotide was synthesised by conventional procedures as described in Example 4), but using a conventional support having an adenine containing nucleoside attached thereto. The sequence of this oligonucleotide was: (5') AAAA (3').

Thus, the second oligonucleotide is of identical length and sequence to the product expected from using the support of the invention and removal of the terminal phosphate from the example described above.

Cleavage of the cleavable link and removal of the terminal (3') phosphate was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with the same retention time as that due to the oligonucleotide with four residues (three phosphates) prepared by conventional methods on a conventional support indicated that the products from using the conventional support and the support from Example 3) were the same.

EXAMPLE 6

Cleavage of an oligonucleotide from the support using aqueous methylamine.

The method of Example 5) was repeated, except that the detritylated oligonucleotide sequence was not cleaved from the solid support by treatment with ammonium hydroxide (sp.gr. 0.88) on the synthesiser, but instead was cleaved from the solid support by the following method.

To each end of the synthesis column containing the detritylated oligonucleotide bound to the solid support was attached a polypropylene syringe. Into one of these syringes was added a solution of methylamine in water (40% methylamine, 2 ml) and the solution was passed through the column and collected in the syringe at the other end. This passage of the alkaline solution through the column was repeated several times over the course of one hour at room temperature, after which the solution was then decanted into a collection vial and incubated at 60° C. for 16 hours.

Cleavage of the cleavable link and removal of the terminal (3') phosphate was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with the same retention time as that due to the oligonucleotide with four residues (three phosphates) prepared by conventional methods on a conventional support indicated that the products from using the conventional support and the support from Example 3) were the same, and that cleavage of the oligonucleotide from the support from Example 3) by conventional methods and by the method described above were the same.

EXAMPLE 7

Cleavage of an oligonucleotide from the support using ethanolic ethylenediamine.

The method of Example 5) was repeated, except that the detritylated oligonucleotide sequence was not cleaved from the solid support by treatment with ammonium hydroxide (sp.gr. 0.88) on the synthesiser, but instead was cleaved from the solid support by the following method.

To each end of the synthesis column containing the detritylated oligonucleotide bound to the solid support was attached a polypropylene syringe. Into one of these syringes was added a solution of ethylenediamine in ethanol (50% ethylenediamine, 2 ml) and the solution was passed through the column and collected in the syringe at the other end. This passage of the alkaline solution through the column was repeated several times over the course of one hour at room temperature, after which the solution was then decanted into a collection vial and incubated at 60° C. for 16 hours.

Cleavage of the cleavable link and removal of the terminal (3') phosphate was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with the same retention time as that due to the oligonucleotide with four residues (three phosphates) prepared by conventional methods on a conventional support indicated that the products from using the conventional support and the support from Example 3) were the same, and that cleavage of the oligonucleotide from the support from Example 3) by conventional methods and by the method described above were the same.

EXAMPLE 8

Cleavage of an oligonucleotide from the support using methanolic triethylamine.

The method of Example 5) was repeated, except that the detritylated oligonucleotide sequence was not cleaved from the solid support by treatment with ammonium hydroxide (sp.gr. 0.88) on the synthesiser, but instead was cleaved from the solid support by the following method.

To each end of the synthesis column containing the detritylated oligonucleotide bound to the solid support was attached a polypropylene syringe. Into one of these syringes was added a solution of triethylamine in methanol (50% triethylamine, 2 ml) and the solution was passed through the column and collected in the syringe at the other end. This passage of the alkaline solution through the column was repeated several times over the course of one hour at room temperature, after which the solution was then decanted into a collection vial and incubated at 60° C. for 16 hours.

Cleavage of the cleavable link and removal of the terminal (3') phosphate was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with the same retention time as that due to the oligonucleotide with four residues (three phosphates) prepared by conventional methods on a conventional support indicated that the products from using the conventional support and the support from Example 3) were the same, and that cleavage of the oligonucleotide from the support from Example 3) by conventional methods and by the method described above were the same.

EXAMPLE 9

Cleavage of an oligonucleotide from the support using aqueous piperidine.

The method of Example 5) was repeated, except that the detritylated oligonucleotide sequence was not cleaved from the solid support by treatment with ammonium hydroxide (sp.gr. 0.88) on the synthesiser, but instead was cleaved from the solid support by the following method.

To each end of the synthesis column containing the detritylated oligonucleotide bound to the solid support was attached a polypropylene syringe. Into one of these syringes was added a solution of piperidine in water 10% piperidine, 2 ml) and the solution was passed through the column and collected in the syringe at the other end. This passage of the alkaline solution through the column was repeated several times over the course of one hour at room temperature, after which the solution was then decanted into a collection vial and incubated at 60° C. for 16 hours.

Cleavage of the cleavable link and removal of the terminal (3') phosphate was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with the same retention time as that due to the oligonucleotide with four residues (three phosphates) prepared by conventional methods on a conventional support indicated that the products from using the conventional support and the support from Example 3) were the same, and that cleavage of the oligonucleotide from the support from Example 3) by conventional methods and by the method described above were the same.

EXAMPLE 10

Cleavage of an oligonucleotide from the support using methanolic sodium hydroxide.

The method of Example 5) was repeated, except that the detritylated oligonucleotide sequence was not cleaved from the solid support by treatment with ammonium hydroxide (sp.gr. 0.88) on the synthesiser, but instead was cleaved from the solid support by the following method.

To each end of the synthesis column containing the detritylated oligonucleotide bound to the solid support was attached a polypropylene syringe. Into one of these syringes was added a 0.5 molar solution of sodium hydroxide in a mixture of methanol and water (1/1, 2 ml) and the solution was passed through the column and collected in the syringe at the other end. This passage of the alkaline solution through the column was repeated several times over the course of one hour at room temperature, after which the solution was then decanted into a collection vial and incubated at room temperature for 16 hours.

Cleavage of the cleavable link and removal of the terminal (3') phosphate was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with the same retention time as that due to the oligonucleotide with four residues (three phosphates) prepared by conventional methods on a conventional support indicated that the products from using the conventional support and the support from Example 3) were the same, and that cleavage of the oligonucleotide from the support from Example 3) by conventional methods and by the method described above were the same.

EXAMPLE 11

Synthesis of oligoribonucleotides using the support from Example 2)

Four fully protected oligoribonucleotides of sequence:

i) (5') UUUU (3')

ii) (5') GGGG (3')

iii) (5') AAAA (3')

iv) (5') CCCC (3')

were prepared as follows.

For each oligoribonucleotide, a column containing the product from Example 2) (3 mg) was attached to an Applied Biosystems 380B DNA synthesiser and the oligomers whose sequences are shown above were synthesised in a stepwise manner from ribonucleoside phosphoramidites, as fully described in the protocol supplied by Cruachem Ltd. for use with their reagents.

The ribonucleoside phosphoramidites used were the 2'-(1-[2-fluorophenyl]-4-methoxypiperidin-1-yl)-3'-(2-cyanoethyl-N,N-diisopropylamino) phosphoramidites of 5'-dimethoxytrityl-$N^4$-benzoylcytidine 5'-dimethoxytrityl-$N^2$-isobutyrylguanosine 5'-dimethoxytrityl-$N^6$-benzoyladenosine and 5'-dimethoxytrityluridine (Cruachem Ltd.).

The duration of the reaction steps and the volume of reagents used for detritylation, activation of nucleoside phosphoramidites, addition of phosphoramidites, capping and oxidation were identical for each coupling, including that for detritylation of the derivatised support and coupling of the first ribonucleotide.

The detritylated oligoribonucleotide sequences were cleaved from the solid support by treatment with ammonium hydroxide (sp.gr. 0.88) on the synthesiser, and the ammoniacal solution was washed into a collection vial according to normal synthesiser protocols. Deprotection and removal of the terminal 3'-phosphate were performed by incubation of this solution at 60° C. for 16 hours.

After this treatment, the solutions were lyophilised and the residues dissolved in an aqueous solution of hydrochloric acid (0.01M, 1 ml) and allowed to stand at room temperature for 16 hours.

Four other oligoribonucleotides of sequence:

i) (5') UUUU (3')

ii) (5') GGGG (3')

iii) (5') AAAA (3')

iv) (5') CCCC (3')

were prepared by conventional procedures as described above but using conventional supports having a uracil, cytosine, guanine, or adenine containing ribonucleoside respectively, attached thereto.

Thus, these oligoribonucleotides are of identical length and sequence to the products expected from using the support of the invention and removal of the terminal phosphate from the examples described above.

Cleavage of the cleavable link and removal of the terminal (3') phosphate was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with the same retention time as that due to the oligoribonucleotide with four residues (three phosphates) prepared by conventional methods on a conventional support indicated that the products from using the conventional support and the support from Example 2) were the same.

EXAMPLE 12

Synthesis of an oligodeoxyribonucleotide with a non-nucleosidic 3'-terminus using the support from Example 2)

A fully protected oligodeoxyribonucleotide of sequence:

(5') TTTT $C_{16}$-SPACER (3')

was prepared using the method of Example 5), except that in place of a column containing the product from Example 3), there was used a column containing the product from Example 2), wherein $C_{16}$-SPACER is a group of structure:

introduced into the oligonucleotide by means of the fully protected phosphoramidite:

in which DMT and PA are as hereinbefore described.

The duration of the reaction steps and the volume of reagents used for detritylation, activation of nucleoside phosphoramidites, addition of phosphoramidites, capping and oxidation were identical for each coupling, including that for detritylation of the derivatised support and coupling of the DMT—O—$(CH_2)_{16}$—O—PA.

The detritylated oligonucleotide sequence was cleaved from the solid support by treatment with ammonium hydroxide (sp.gr. 0.88) on the synthesiser, and the ammoniacal solution was washed into a collection vial according to normal synthesiser protocols. Deprotection and removal of the terminal 3'-phosphate were performed by incubation of this solution at 60° C. for 16 hours.

A second oligonucleotide of sequence:

(5') $C_{16}$-SPACER TTTT (3')

was synthesised by conventional procedures as described above, but using a conventional support having a thymine containing nucleoside attached thereto, and by using the DMT—O—$(CH_2)_{16}$—O—PA as the last coupling in the synthesis.

Cleavage of the cleavable link and removal of the terminal (3') phosphate was demonstrated by analysis of the products of the reaction on ion exchange HPLC according to the method of Example 5). The presence of a peak with the same retention time as that due to the oligonucleotide with the $C_{16}$-SPACER moiety at the 5'-terminus indicated that the non-nucleosidic 3'-terminus, $C_{16}$-SPACER, had been introduced into the oligonucleotide by means of the support from Example 2)

EXAMPLE 13

Preparation of Reagent A2

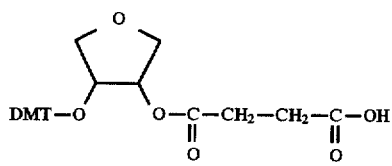

DMT is 4,4'dimethyoxytrityl.
Step 1 - Preparation of:

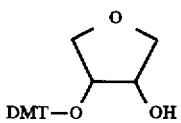

To a solution of 1,4-anhydroerythritol (10.4 g, 100 mmol) in dry pyridine (100 ml) at 0° C., benzoyl chloride (14 g, 100 mmol) was added dropwise with stirring. When addition was complete, the solution was allowed to warm to room temperature and stirring was maintained for a further two hours. To this solution was added 4,4'-dimethoxytrityl chloride (37.4 g, 110 mmol) and 4-N,N-dimethylaminopyridine (100 mg) and the mixture was stirred at room temperature for 16 hours. The solvent was removed by rotary evaporation and the residue redissolved in dichloromethane and washed three times with saturated sodium bicarbonate solution. The dichloromethane solution was dried by the addition of anhydrous sodium sulphate and filtered. The filtrate was evaporated to a gum and redissolved in methanol saturated with methylamine. The resultant solution was incubated at room temperature until no starting material could be detected by TLC. The solvent was removed by rotary evaporation, and the residue redissolved in the minimum volume of dichloromethane/methanol (9/1) and loaded on a silica chromatography column. Elution with the same solvent gave the title compound as a white foam (22 g, 54%).
$^1$H NMR: ($\delta$, CDCl$_3$): 3.35, 1H, multiplet, C$\underline{H}$OH; 3.5, 2H, doublet, —CH$_2$—; 3.75, 8H, complex multiplet, 2×—OCH$_3$ and —CH$_2$—; 4.2, 1H, complex multiplet, DMT-OC$\underline{H}$; 6.9, 4H, complex multiplet, aromatics; 7.25–7.5, 9H, complex multiplet, aromatics.

Step 2

The product from step 1 (10 g, 24.6 mmol) was dissolved in dry pyridine (150 ml) and succinic anhydride (10 g, 100 mmol) was added. When dissolution was complete, 4-(N, N-dimethylamino)pyridine (500 mg) was added and the solution was stirred at room temperature overnight. The solvent was evaporated under reduced pressure and residual pyridine removed by repeated co-evaporation with toluene. The residue was redissolved in dichloromethane (500 ml) and washed three times with ice cold 10% citric acid solution. The organic layer was separated, dried (sodium sulphate) filtered and evaporated to a gum which was redissolved in the minimum volume of dichloromethane/methanol (9/1) and loaded on a silica chromatography column. Elution with the same solvent gave the title compound as a white foam (9.7 g, 78%).

$^1$H NMR: ($\delta$, CDCl$_3$): 2.75, 4H, multiplet, 2×COCH$_2$; 2.9 and 3.2, 2H two pseudo triplets, —CH$_2$—; 3.75, 8H , complex multiplet, 2×—OCH$_3$ and —CH$_2$—;4.2, 1H, complex multiplet, DMT-OCH; 5.0, 1H, multiplet, CHOCO 6.9, 4H, complex multiplet, aromatics; 7.25–7.5, 9H, complex multiplet, aromatics.

EXAMPLE 14

Coupling of Reagent A2 to controlled pore glass

The method of Example 2) was repeated, except that in place of Reagent A1 there was used Reagent A2.

The extent of loading of the support with Reagent A2) was determined by the method of Example 2). By this method, the loading of the support with Reagent A2) was 15 μmole/g.

The resultant product was a support carrying a group of Formula:

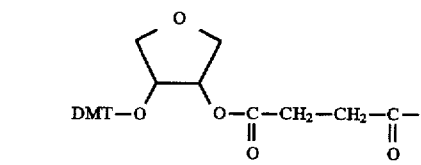

As will be appreciated, the right hand side is connected to CPG via an organic spacer group.

Example 15

Synthesis of an oligonucleotide using the support from Example 14)

The method of Example 5was repeated, except that in place of a column containing the product from Example 3), there was used a column containing the product from Example 14).

The presence of a peak with the same retention time as that due to the oligonucleotide with four residues (three phosphates) prepared by conventional methods on a conventional support indicated that the products from using the conventional support and the support from Example 14) were the same.

EXAMPLE 16

Preparation of Reagent A4)

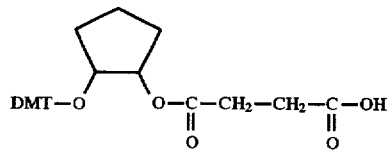

To a solution of cyclopentane-cis-1,2-diol (0.5 g, 4.9 mmol) in dry pyridine (10 ml) were added 4,4'-dimethoxytrityl chloride (1.94 g, 5.76 mmol), succinic anhydride (0.5 g, 5 mmol) and DMAP (0.4 g), and the solution was left to stand at room temperature for 48 hours. The solvent was removed by rotary evaporation and residual pyridine was removed by repeated co-evaporation with toluene. The residue was redissolved in dichloromethane (100 ml) and washed with an ice cold solution of citric acid in water (10%, 3×100 ml). The organic layer was separated, dried (MgSO$_4$), filtered and evaporated to a foam, which was redissolved in the minimum volume of dichloromethane:methanol (9:1) and applied to a silica column. Elution with the same solvent gave the title compound as a pale yellow foam (0.5 g, 20%).
$^1$H NMR: $\delta$(CDCl$_3$): 1.1–2.0 (6H, m, —C$\underline{H}_2$C$\underline{H}_2$C$\underline{H}_2$—); 2.75 (4H, m, 2×—C$\underline{H}_2$CO); 3.8 (6H, s, 2×OC$\underline{H}_3$); 4.25 (1H, m, DMT—OC$\underline{H}$); 5.0 (1H, m, C$\underline{H}$OCO); 6.9 (4H, m, aromatics); 7.1–7.6 (9H, m, aromatics).

EXAMPLE 17

Coupling of Reagent A4 to controlled pore glass

The method of Example 2) was repeated, except that in place of Reagent A1 there was used Reagent A4.

The extent of loading of the support with Reagent A4) was determined by the method of Example 2). By this method, the loading of the support with Reagent A4) was 19 µmole/g.

The resultant product was a support carrying a group of Formula:

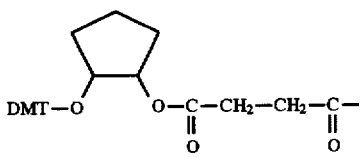

As will be appreciated, the right hand side is connected to CPG via an organic spacer group.

EXAMPLE 18

Synthesis of an oligonucleotide using the support from Example 20)

The method of Example 5) was repeated except that in place of a column containing the product from Example 3), there was used a column containing the product from Example 20).

Cleavage of the cleavable link and removal of the terminal (3') phosphate was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with the same retention time as that due to the oligonucleotide with four residues (three phosphates) prepared by conventional methods on a conventional support indicated that the products from using the conventional support and the support from Example 20) were the same.

EXAMPLE 19

Preparation of Reagent A5

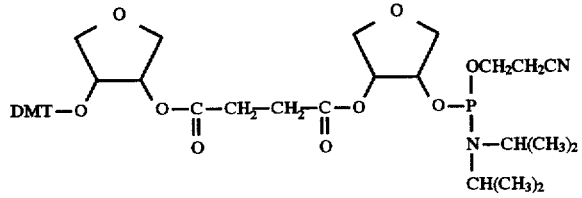

Step 1—Preparation of:

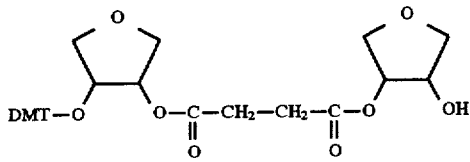

Reagent A2 from Example 13, step 2 (10 g, 19.5 mmol) was dissolved in dry pyridine (200 ml) containing 1,4-anhydroerythritol (10.4 g, 100 mmol). To this solution was added 1-(3-dimethylaminopropyl)-3-ethyl carbodiimide hydrochloride (Aldrich, 3.75 g, 19.5 mmol). The solution was stirred at room temperature overnight when TLC in dichloromethane:methanol (19:1) showed there to be no starting material present. The solvent was removed under reduced pressure and residual pyridine removed by repeated co-evaporation with toluene. The residue was redissolved in ethyl acetate and washed three times with saturated sodium bicarbonate solution and once with water. The organic layer was separated, dried (sodium sulphate), filtered and evaporated under reduced pressure to give a gum which was redissolved in the minimum volume of dichloromethane:methanol (19:1) and loaded on a silica chromatography column. Elution with the same solvent gave the title compound as a colourless gum (9.5 g, 79%). $^1$H NMR: (δ, CDCl$_3$): 2.75–2.9, 5H, multiplet, 2×COCH$_2$ +—OH; 3.2, 2H, multiplet, —CH$_2$—; 3.65–3.85, 10H, complex multiplet, 2×—OCH$_3$ and 2×—CH$_2$—; 3.9–4.1, 2H, multiplet, —CH$_2$—; 4.2, 1H, complex multiplet, DMT—O—CH; 4.4, 1H, multiplet, CHOH; 5.0 and 5.1, 2H, two multiplets, 2×CHOCO; 6.9, 4H, complex multiplet, aromatics; 7.25–7.5, 9H, complex multiplet, aromatics.

Step 2—Preparation of Reagent A5

The product from step 1 (2g, 3.3 mmol) was dissolved in dry dichloromethane (50 ml) and the solution stirred under a stream of dry argon. To this solution was added dry diisopropylethylamine (2.7 ml, 16 mmol) and 2-cyanoethyl-N,N diisopropylamino- chlorophosphine (1.05 ml, 4.72 mmol). The solution was stirred at room temperature under a stream of dry argon for 30 minutes when TLC in dichloromethane:triethylamine (19:1) showed there to be no starting material present. The reaction was quenched by addition of dry methanol (5 ml) and the solution was diluted with ethyl acetate (200 ml). This solution was washed with three equal volumes of saturated sodium chloride solution, and one volume of water. The organic layer was separated, dried (sodium sulphate), filtered and evaporated under reduced pressure to a gum which was redissolved in the minimum volume of dichloromethane:triethylamine (19:1) and loaded on a silica chromatography column. Elution with the same solvent gave the title reagent A1 as a colourless gum (1.8 g, 65%).

Step 3

Reagent A5 may be condensed with a support comprising a carrier and an organic spacer group having a terminal amino group or a terminal hydroxy group by 1. activating reagent A5 with tetrazole; 2. condensing the product with the support; 3. capping with acetic anhydride; and 4. oxidation using H$_2$O/I$_2$.

EXAMPLE 20

Preparation of Reagent A6

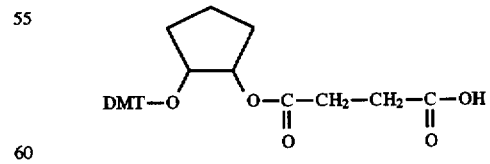

To a solution of cyclopentane-trans-1,2-diol (0.5 g, 4.9 mmol) in dry pyridine (10 ml) were added 4,4'-dimethoxytrityl chloride (1.94 g, 5.76 mmol), succinic anhydride (0.5 g, 5 mmol) and DMAP (0.4 g), and the solution was left to stand at room temperature for 48 hours. The solvent was removed by rotary evaporation and residual pyridine was removed by repeated co-evaporation with toluene. The residue was redissolved in dichloromethane (100 ml) and washed with an ice cold solution of citric acid in water (10%, 3×100 ml). The organic layer was separated, dried (MgSO$_4$), filtered and evaporated to a foam, which was redissolved in the minimum volume of dichloromethane:methanol (9:1) and applied to a silica column. Elution with the same solvent gave the title compound as a yellow foam (0.6 g, 24 %).

$^1$H NMR: δ(CDCl$_3$): 1.1–2.0 (6H, m, —CH$_2$CH$_2$CH$_2$—); 2.75 (4H, m, 2 ×—CH$_2$CO); 3.8 (6H, s, 2×—OCH$_3$); 4.25 (1H, m, DMT—OCH); 5.0 (1H, m, CHOCO); 6.9 (4H, m, aromatics); 7.1–7.6 (9H, m, aromatics).

EXAMPLE 21

Coupling of Reagent A6 to controlled pore glass

The method of Example 2) was repeated, except that in place of Reagent A1 there was used Reagent A6.

The extent of loading of the support with Reagent A6) was determined by the method of Example 2). By this method, the loading of the support with Reagent A6) was 51 μmole/g.

The resultant product was a support carrying a group of Formula:

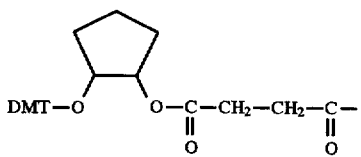

As will be appreciated, the right hand side is connected to CPG via an organic spacer group.

EXAMPLE 22

Synthesis of an oligonucleotide using the support from Example 24)

The method of Example 5) was repeated except that in place of a column containing the product from Example 3), there was used a column containing the product from Example 24).

Cleavage of the clearable link was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with a longer retention time than that due to the control oligonucleotide with four residues (three phosphates) prepared by conventional methods on a conventional support indicated that removal of the terminal (3') phosphodiester moiety from the oligonucleotide prepared using the support from Example 24) had not occurred under these conditions.

EXAMPLE 23

Preparation of Reagent A7

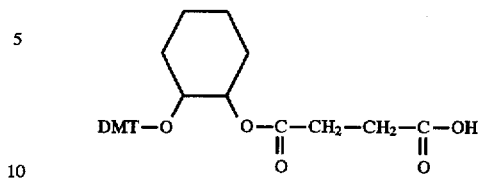

To a solution of cyclohexane-cis-1,2-diol (0.57 g, 4.9 mmol) in dry pyridine (10 ml) were added 4,4'-dimethoxytrityl chloride (1.94 g, 5.76 mmol), succinic anhydride (0.5 g, 5 mmol) and DMAP (0.4 g), and the solution was left to stand at room temperature for 48 hours. The solvent was removed by rotary evaporation and residual pyridine was removed by repeated co-evaporation with toluene. The residue was redissolved in dichloromethane (100 ml) and washed with an ice cold solution of citric acid in water (10 %, 3×100 ml). The organic layer was separated, dried (MgSO$_4$), filtered and evaporated to a foam, which was redissolved in the minimum volume of dichloromethane:methanol (9:1) and applied to a silica column. Elution with the same solvent gave the title compound as a yellow foam (0.44 g, 17.3%).

$^1$H NMR: δ(CDCl$_3$): 0.9–1.0 (2H, m, —CH$_2$—); 1.2–1.9 (6H, m, —CH$_2$CH$_2$CH$_2$—); 2.75 (4h, m, 2×—CH$_2$CO); 3.6 (1H, m, DMT-OCH); 3.9 (6H, s, 2×—OCH$_3$); 4.85 (1H, m, —CHOCO—); 6.9 (4H, m, aromatics); 7.2–7.9 (9H, m, aromatics).

EXAMPLE 24

Coupling of Reagent A7 to controlled pore glass

The method of Example 2) was repeated, except that in place of Reagent A1 there was used Reagent A7.

The extent of loading of the support with Reagent A7) was determined by the method of Example 2). By this method, the loading of the support with Reagent A7) was 46 μmole/g.

The resultant product was a support carrying a group of Formula:

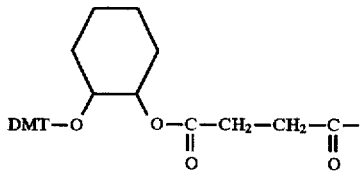

As will be appreciated, the right hand side is connected to CPG via an organic spacer group.

EXAMPLE 25

Synthesis of an oligonucleotide using the support from Example 24)

The method of Example 5) was repeated except that in place of a column containing the product from Example 3), there was used a column containing the product from Example 27).

Cleavage of the cleavable link was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with a longer retention time than that due to the control oligonucleotide with four residues (three phosphates) prepared by conventional methods on a conventional support indicated that removal of the terminal (3') phosphodiester moiety from the oligonucleotide prepared using the support from Example 27) had not occurred under these conditions.

EXAMPLE 26

Preparation of Reagent A8

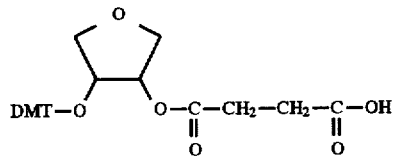

To a solution of 1,4-anydrothreitol (0.5 g, 4.8 mmol) in dry pyridine (10 ml) were added 4,4'-dimethoxytrityl chloride (1.94 g, 5.76 mmol), succinic anhydride (0.5 g, 5 mmol) and DMAP (0.4 g), and the solution was left to stand at room temperature for 48 hours. The solvent was removed by rotary evaporation and residual pyridine was removed by repeated co-evaporation with toluene. The residue was redissolved in dichloromethane (100 ml) and washed with an ice cold solution of citric acid in water (10 %, 3×100 ml). The organic layer was separated, dried (MgSO$_4$), filtered and evaporated to a foam, which was redissolved in the minimum volume of dichloromethane:methanol (9:1) and applied to a silica column. Elution with the same solvent gave the title compound as a pale yellow gum (0.5 g, 20%).

$^1$H NMR: δ(CDCl$_3$): 2.75 (4H, m, 2×—CH$_2$CO); 3.0–3.2 (2H, m, —C$\underline{H}_2$—); 3.75 (8H, m, 2×—O$\overline{C}$H$_3$ and —C$\underline{H}_2$—); 4.2 (1H, m, DMT-OC$\underline{H}$); 5.0 (1H, m, C$\underline{H}$OCO); 6.9 (4H, m, aromatics); 7.2–7.5 (9H, m, aromatics).

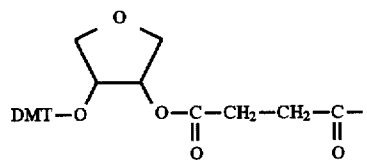

As will be appreciated, the right hand side is connected to CPG via an organic spacer group.

EXAMPLE 28

Synthesis of an oligonucleotide using the support from Example 30)

The method of Example 5) was repeated except that in place of a column containing the product from Example 3), there was used a column containing the product from Example 30).

Cleavage of the cleavable link was demonstrated by analysis of the products of the reaction by ion-exchange HPLC on a Pharmacia Mono-Q column using a linear gradient of 0–45% buffer B in buffer A over 35 minutes, where buffer A was 50 mM Tris.chloride (pH 7.5), and buffer B was 50 mM Tris.chloride/800 mM sodium chloride (pH 7.5).

The presence of a peak with a longer retention time than that due to the control oligonucleotide with four residues (three phosphates) prepared by conventional methods on a conventional support indicated that removal of the terminal (3') phosphodiester moiety from the oligonucleotide prepared using the support from Example 30) had not occurred under these conditions.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 25 base pairs
      ( B ) TYPE: nucleic acid
      ( C ) STRANDEDNESS: both
      ( D ) TOPOLOGY: linear ( i i ) MOLECULE TYPE: DNA (genomic)

( x i ) SEQUENCE DESCRIPTION: SEQ ID NO:1:

CAAGTTTTCA GTCAGCCGAG TTCAG    2 5

---

EXAMPLE 27

Coupling of Reagent A8 to controlled pore glass

The method of Example 2) was repeated, except that in place of Reagent A1 there was used Reagent A8.

The extent of loading of the support with Reagent A8) was determined by the method of Example 2). By this method, the loading of the support with Reagent A8) was 11 μmole/g.

The resultant product was a support carrying a group of Formula:

We claim:

1. A support carrying a cyclopentyl ring, a cyclohexyl ring or a heterocyclic ring consisting of 4 or 5 carbon atoms and 1 nitrogen, sulphur or oxygen atom, said ring including a first and a second carbon atom wherein:

(i) said first carbon atom is substituted by a nucleophilic group selected from the class consisting of an amino group, a thio group and a hydroxy group, or an ester group convertible to a nucleophilic group on treatment with base;

(ii) said second carbon atom is substituted by a hydroxy group protected by an acid labile protecting group, or a phosphate group substituted by an oligonucleotide;

(iii) the first and second carbon atoms are directly connected to one another by a covalent bond;

(iv) said ring is coupled to the support through said first carbon atom or through said nucleophilic group or group convertible to said nucleophilic group on said first carbon atom; and (v) said ring optionally being further substituted on any one or more carbon atom other than said first and second carbon atoms.

2. A support according to claim 1 wherein the support carries a group of formula (2)

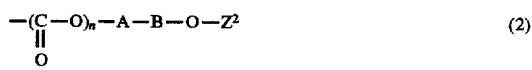
(2)

wherein A and B are said first and second carbon atoms, respectively;

$Z^2$ is an acid labile protecting group, or a phosphate group substituted by an oligonucleotide; and n is 1.

3. A support according to claim 1 or 2 wherein said heterocyclic ring is a pyran or furan ring free from double bonds.

4. A support according to claim 1 or 2 wherein said one or more optional ring carbon substituent is independently selected from hydroxy; a group convertible to hydroxy on treatment with base; straight or branched chain $C_{1-6}$alkyl; $C_{1-6}$alkoxy; aryloxy; halogen; cyano; and nitro.

5. A support according to claim 2 wherein $Z^2$ is an acid labile protecting group selected from the group consisting of tetrahydropyranyl groups; optionally substituted trityl groups; pixyl; isobutyloxycarbonyl; t-butyl; and dimethylsilyl.

6. A support according to claim 5 wherein $Z^2$ is monomethoxytrityl or dimethoxytrityl.

7. A support according to claim 2 wherein:

A and B are carbon atoms of an optionally substituted 5- or 6-membered ring selected from pyran and furan rings free from double covalent bonds, and cyclohexyl and cyclopentyl rings;

$Z^2$ is monomethoxytrityl or dimethoxytrityl;

n is 1; and said one or more optional ring carbon substituent is independently selected from hydroxy; straight and branched chain $C_{1-6}$alkyl; $C_{1-6}$alkoxy; aryloxy; halogen; cyano; nitro; thio; and amino.

8. A support according to claim 2 wherein the group of Formula (2) is selected from formulae 1(b), 1(c) and 1(d):

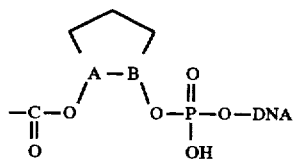
(1b)

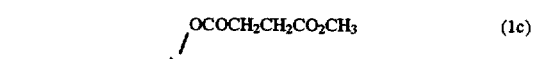
(1c)

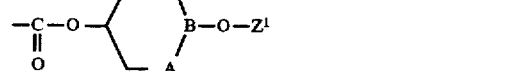
(1d)

wherein A is said first carbon atom; B is said second carbon atom, and $Z^1$ is an acid labile protecting group.

9. A support carrying a group selected from the formulae

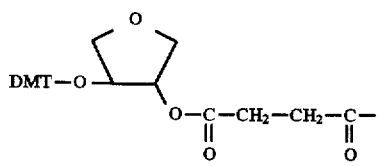

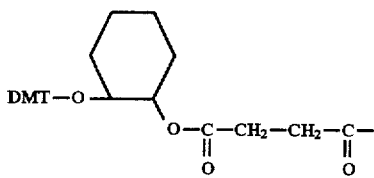

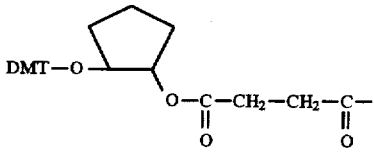

and

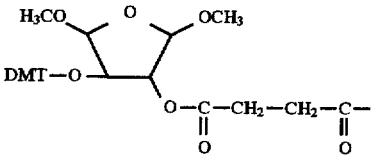

wherein DMT is 4,4'-dimethoxytrityl.

* * * * *